US012559445B2

(12) United States Patent
Harandi et al.

(10) Patent No.: US 12,559,445 B2
(45) Date of Patent: Feb. 24, 2026

(54) PROCESSES AND SYSTEMS FOR UPGRADING A HYDROCARBON-CONTAINING FEED

(71) Applicant: EXXONMOBIL CHEMICAL PATENTS INC., Baytown, TX (US)

(72) Inventors: Mohsen N. Harandi, Calgary (CA); Paul F. Keusenkothen, Houston, TX (US); Ying Liu, Houston, TX (US)

(73) Assignee: EXXONMOBIL CHEMICAL PATENTS INC., Baytown, TX (US)

( * ) Notice: Subject to any disclaimer, the term of this patent is extended or adjusted under 35 U.S.C. 154(b) by 238 days.

(21) Appl. No.: 18/254,260

(22) PCT Filed: Nov. 17, 2021

(86) PCT No.: PCT/US2021/059707
§ 371 (c)(1),
(2) Date: May 24, 2023

(87) PCT Pub. No.: WO2022/132369
PCT Pub. Date: Jun. 23, 2022

(65) Prior Publication Data
US 2024/0010581 A1 Jan. 11, 2024

Related U.S. Application Data

(60) Provisional application No. 63/126,104, filed on Dec. 16, 2020.

(51) Int. Cl.
*C07C 2/12* (2006.01)
*C10G 55/06* (2006.01)

(52) U.S. Cl.
CPC ............... *C07C 2/12* (2013.01); *C10G 55/06* (2013.01)

(58) Field of Classification Search
CPC .. C07C 2/12; C10G 55/06; C10G 9/32; C10G 45/02; C10G 50/00; C10G 69/126; C10J 2300/0943; C10J 2300/0956; C10J 2300/0976; C10J 2300/16; C10J 2300/1823; C10J 3/00; B01J 29/40;
(Continued)

(56) References Cited

U.S. PATENT DOCUMENTS

| | | | |
|---|---|---|---|
| 4,675,098 A | 6/1987 | Miyauchi et al. | |
| 4,935,568 A * | 6/1990 | Harandi | C10G 3/57 585/329 |

(Continued)

FOREIGN PATENT DOCUMENTS

WO 2017/127288 7/2017

*Primary Examiner* — In Suk C Bullock
*Assistant Examiner* — Jason Y Chong
(74) *Attorney, Agent, or Firm* — WOMBLE BOND DICKINSON (US) LLP; Kevin Davis

(57) ABSTRACT

Processes for upgrading a hydrocarbon-containing feed. The feed and a first particle stream can be contacted under pyrolysis conditions to effect pyrolysis of the feed to produce a pyrolysis effluent that can include olefins and the particles, where coke can be formed on the particles. A first gaseous stream and a second particle stream can be obtained from the pyrolysis effluent. At least a portion of the first gaseous stream can be contacted with oligomerization catalyst particles under oligomerization conditions to effect oligomerization of at least a portion of olefins in the first gaseous stream.

24 Claims, 1 Drawing Sheet

(58) Field of Classification Search
　　 CPC ........ B01J 29/46; B01J 29/90; B01J 2229/10;
　　　　　　　 Y02P 20/52; Y02P 20/584; C10B 55/04;
　　　　　　　 C10B 55/10; C10B 57/02; C10K 1/004
　　 See application file for complete search history.

(56)　　　　　　　　　 References Cited

U.S. PATENT DOCUMENTS

| | | | |
|---|---|---|---|
| 5,000,837 A * | 3/1991 | Harandi | C10G 11/18 208/147 |
| 8,486,258 B2 * | 7/2013 | Podrebarac | C10L 1/04 208/209 |
| 10,407,631 B2 | 9/2019 | Harandi et al. | |
| 2019/0144756 A1 | 5/2019 | Le et al. | |

* cited by examiner

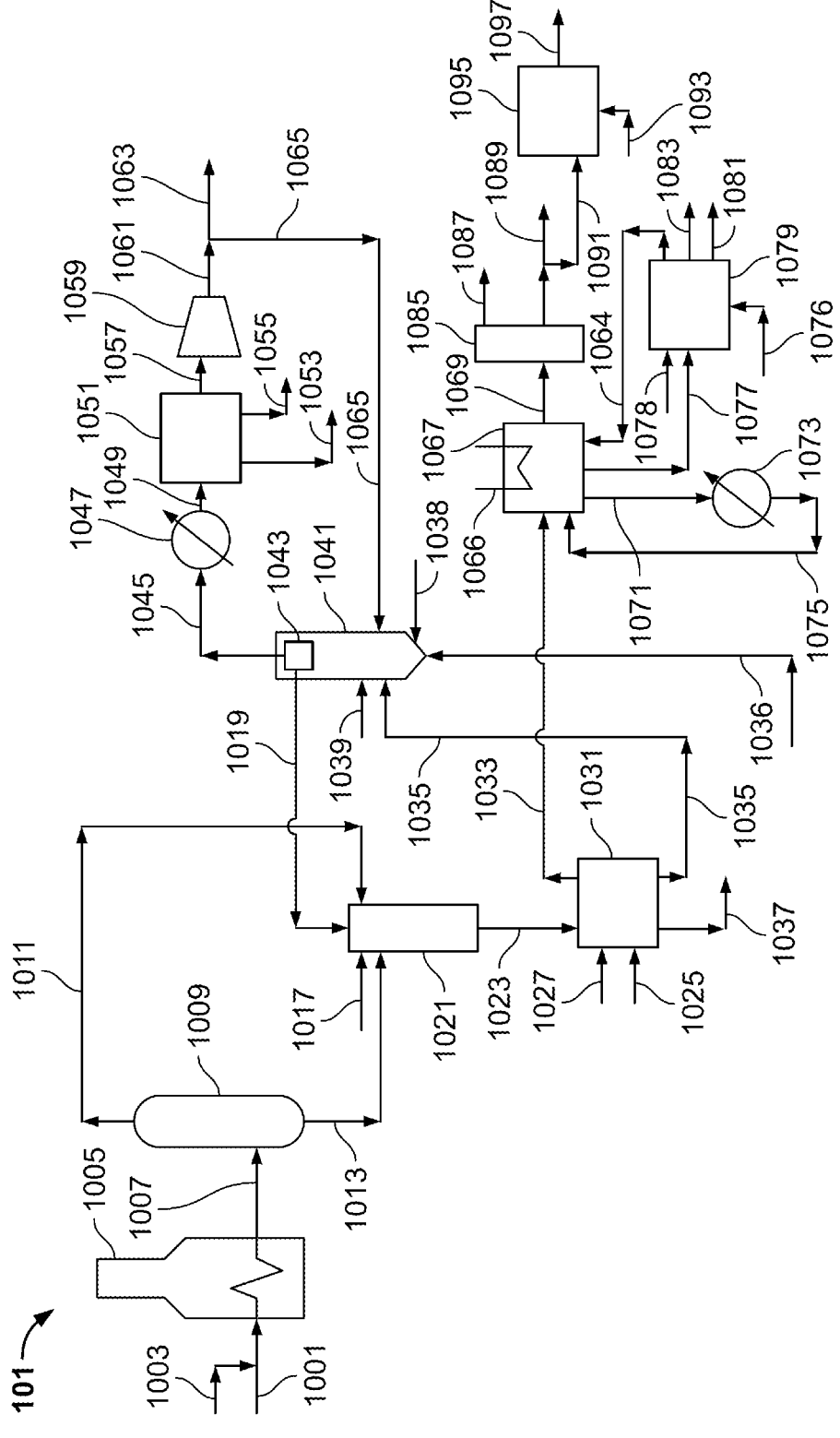

PROCESSES AND SYSTEMS FOR UPGRADING A HYDROCARBON-CONTAINING FEED

CROSS-REFERENCE TO RELATED APPLICATIONS

This application is a US national phase application of PCT Application Serial No. PCT/US2021/059707 having a filing date of Nov. 17, 2021, which claims priority to and the benefit of U.S. Provisional Application No. 63/126,104 having a filing date of Dec. 16, 2020, the disclosures of both of which are incorporated herein by reference in their entireties.

FIELD

This disclosure relates to processes and systems for upgrading a hydrocarbon-containing feed. In particular, this disclosure relates to processes and systems for upgrading a hydrocarbon-containing feed by pyrolysis and gasification/combustion to produce olefins and oligomerizing at least a portion of the olefins.

BACKGROUND

Steam cracking, also referred to as pyrolysis, has long been used to crack various hydrocarbon-containing feeds into olefins, preferably light olefins such as ethylene, propylene, and butenes. Conventional steam cracking utilizes a pyrolysis furnace ("steam cracker") that has two main sections: a convection section and a radiant section. The hydrocarbon-containing feed typically enters the convection section of the furnace as a liquid (except for light feedstocks that typically enter as a vapor) where the feedstock is typically heated and vaporized by indirect heat exchange with a hot flue gas from the radiant section and by direct contact with steam. The vaporized feedstock and steam mixture is fed into the radiant section where the cracking takes place. The resulting pyrolysis effluent, including olefins, leaves the pyrolysis furnace for further downstream processing, including quenching.

Conventional pyrolysis furnaces do not have the flexibility to process residues, crudes, or many residues, crude gas oils, or naphthas that are contaminated with non-volatile components. Non-volatile components, if present in the feed, typically cause fouling within the radiant section of the pyrolysis furnace. An external vaporization drum or flash drum has been implemented to separate vaporized hydrocarbons from liquid hydrocarbons to address the fouling problems in the pyrolysis furnace. The vaporized hydrocarbons are then cracked in the pyrolysis furnace and the liquid hydrocarbons that include nonvolatile components are removed and used as fuel. The liquid hydrocarbons, however, still contain a substantial quantity of hydrocarbons which, if converted into higher-value lighter hydrocarbons such as olefins via cracking, would bring substantial additional value to the crude oil feed. Thus, for decades the petrochemical industry has been trying to take advantage of relatively low-cost heavy crude oil to make substantial quantities of valuable chemicals such as olefins. The large amount of non-volatiles in the low-cost heavy crude oil, however, requires extensive and expensive processing.

There is a need, therefore, for improved processes and systems for upgrading hydrocarbon-containing feeds to produce valuable chemical products such as olefins. This disclosure satisfies this and other needs.

SUMMARY

The present inventors have devised processes and systems for upgrading a hydrocarbon-containing feed by pyrolysis and gasification/combustion to produce olefins and oligomerizing at least a portion of the olefins in a simple and advantageous manner. The process for upgrading the hydrocarbon-containing feed, can include (I) feeding a hydrocarbon-containing feed stream that can include $C_{2+}$ hydrocarbons into a pyrolysis zone; (II) feeding a first particle stream that can include particles having a pyrolysis temperature into the pyrolysis zone; and (III) contacting the hydrocarbon-containing feed stream with the particles in the pyrolysis zone under pyrolysis conditions to effect pyrolysis of at least a portion of the $C_{2+}$ hydrocarbons to produce a pyrolysis zone effluent that can include olefins and the particles, where coke can be formed on the surface of the particles. The process can also include (IV) obtaining from the pyrolysis zone effluent a first gaseous stream rich in the olefins and a second particle stream rich in the particles; (V) feeding at least a portion of the second particle stream, an oxidant stream, and optionally a first steam stream into a gasification/combustion zone; and (VI) contacting the first particle stream, the oxidant stream, and optionally the first steam stream in the gasification/combustion zone under gasification/combustion conditions to produce a gasification/combustion zone effluent comprising regenerated particles and a gasification/combustion gas mixture. The process can also include (VII) obtaining from the gasification/combustion zone effluent a second gaseous stream rich in the gasification/combustion gas mixture and a third particle stream rich in the regenerated particles; (VIII) feeding at least a portion of the third particle stream into the pyrolysis zone as at least a portion of the first particle stream fed into the pyrolysis zone in step (II). The process can also include (IX) feeding at least a portion of the first gaseous stream into an oligomerization zone; and (X) contacting at least a portion of the first gaseous stream with oligomerization catalyst particles in the oligomerization zone under oligomerization conditions to effect oligomerization of at least a portion of the olefins in the first gaseous stream to produce an oligomerization zone effluent. In some embodiments, the processing scheme disclosed herein can provide the opportunity to switch from olefins production to fuels production or vice versa depending on market pricing and demand.

BRIEF DESCRIPTION OF THE DRAWING

The FIGURE depicts an illustrative system for upgrading a hydrocarbon-containing feed by pyrolysis and gasification to produce olefins and oligomerizing at least a portion of the olefins, according to one or more embodiments described.

DETAILED DESCRIPTION

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

As used herein, the indefinite article "a" or "an" shall mean "at least one" unless specified to the contrary or the context clearly indicates otherwise. Thus, embodiments using "a pyrolysis reactor" include embodiments where one, two or more pyrolysis reactors are used, unless specified to the contrary or the context clearly indicates that only one pyrolysis reactor is used.

The term "hydrocarbon" as used herein means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn-hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

The term "non-volatile components" as used herein refers to the fraction of a petroleum feed having a nominal boiling point of at least 590° C., as measured by ASTM D6352-15 or D-2887-18. Non-volatiles include coke precursors, which are large, condensable molecules that condense in the vapor and then form coke during pyrolysis of the petroleum feed.

The term "crude" as used herein means whole crude oil as it flows from a wellhead, a production field facility, a transportation facility, or other initial field processing facility, optionally including crude that has been processed by a step of desalting, treating, and/or other steps as may be necessary to render it acceptable for conventional distillation in a refinery. Crude, as used herein, is presumed to contain resid. The term "crude fraction", as used herein, means a hydrocarbon fraction obtained via the fractionation of crude.

The term "resid" as used herein refers to a bottoms cut of a crude distillation process that contains non-volatile components. Resids are complex mixtures of heavy petroleum compounds otherwise known in the art as residuum or residual. Atmospheric resid is the bottoms product produced from atmospheric distillation of crude where a typical endpoint of the heaviest distilled product is nominally 343° C., and is referred to as 343° C. resid. The term "nominally", as used herein, means that reasonable experts may disagree on the exact cut point for these terms, but by no more than +/−55.6° C. preferably no more than +/−27.8° C. Vacuum resid is the bottoms product from a distillation column operated under vacuum where the heaviest distilled product can be nominally 566° C., and is referred to as 566° C. resid.

The term "water" refers to the chemical compound having formula $H_2O$ and can be in a solid phase (ice), a liquid phase, or a gaseous phase (steam), depending, at least in part, on the particular process conditions, e.g., temperature and pressure.

The term "olefin product" as used herein means a product that includes an alkene, preferably a product consisting essentially of one or more alkenes. An olefin product in the meaning of this disclosure can be, for example, an ethylene stream, a propylene stream, a butylene stream, an ethylene/propylene mixture stream, and the like.

The term "aromatic" as used herein is to be understood in accordance with its art-recognized scope which includes alkyl substituted and unsubstituted mono- and polynuclear compounds.

The term "consisting essentially of" as used herein means the composition, feed, effluent, product, or other stream includes a given component at a concentration of at least 60 wt %, preferably at least 70 wt %, more preferably at least 80 wt %, more preferably at least 90 wt %, still more preferably at least 95 wt %, based on the total weight of the composition, feed, effluent, product, or other stream in question.

The term "rich" when used in phrases such as "X-rich" or "rich in X" means, with respect to an outgoing stream obtained from a device, that the stream comprises material X at a concentration higher than in the feed material fed to the same device from which the stream is derived.

The term "lean" when used in phrases such as "X-lean" or "lean in X" means, with respect to an outgoing stream obtained from a device, that the stream comprises material X at a concentration lower than in the feed material fed to the same device from which the stream is derived.

The terms "channel" and "line" are used interchangeably and mean any conduit configured or adapted for feeding, flowing, and/or discharging a gas, a liquid, and/or a fluidized solids feed into the conduit, through the conduit, and/or out of the conduit, respectively. For example, a composition can be fed into the conduit, flow through the conduit, and/or discharge from the conduit to move the composition from a first location to a second location. Suitable conduits can be or can include, but are not limited to, pipes, hoses, ducts, tubes, and the like.

As used herein, "wt %" means percentage by weight, "vol %" means percentage by volume, "mol %" means percentage by mole, "ppm" means parts per million, and "ppm wt" "wppm", and "ppm by weight" are used interchangeably to mean parts per million on a weight basis. All concentrations herein are expressed on the basis of the total amount of the composition in question, unless specified otherwise. Thus, the concentrations of the various components of the "hydrocarbon-containing feed" are expressed based on the total weight of the hydrocarbon-containing feed. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

The hydrocarbon-containing feed or simply the hydrocarbon feed can be, can include, or can be derived from petroleum, plastic material, natural gas condensate, landfill gas (LFG), biogas, coal, biomass, bio-based oils, rubber, or any mixture thereof. In some examples, the hydrocarbon-containing feed can include a non-volatile component. In some examples, the petroleum can be or can include any crude or any mixture thereof, any crude fraction or any mixture thereof, or any mixture of any crude with any crude fraction. A typical crude includes a mixture of hydrocarbons with varying carbon numbers and boiling points. Thus, by using conventional atmospheric distillation and vacuum distillation, one can produce a range of fuel products with varying boiling points, for example, naphtha, gasoline, kerosene, distillate, and tar. It is highly desired, however, to convert the large hydrocarbon molecules contained in the crude into more valuable, lighter products including, but not limited, to ethylene, propylene, butylenes, and the like, which can be further made into more valuable products such as polyethylene, polypropylene, ethylene-propylene copolymers, butyl rubbers, and the like.

The petroleum can be or can include: crude oil, atmospheric resid, vacuum resid, steam cracked gas oil and residue, gas oil, heating oil, hydrocrackate, atmospheric pipestill bottoms, vacuum pipestill streams including bottoms, gas oil condensate, heavy non-virgin hydrocarbon stream from refineries, vacuum gas oil, heavy gas oil, naphtha contaminated with crude, heavy residue, $C_4$'s/residue admixture, naphtha/residue admixture, hydrocarbon gases/residue admixture, hydrogen/residue admixture, gas oil/residue admixture, or any mixture thereof. Non-limiting examples of crudes can be, or can include, but are not limited to, Tapis, Murban, Arab Light, Arab Medium, and/or Arab Heavy.

In some embodiments, the hydrocarbon-containing feed can include, but is not limited to, one or more $C_2$-$C_5$ alkanes. In some embodiments, the hydrocarbon-containing feed can include, but is not limited to, one or more $C_2$-$C_5$ alkanes at a total concentration of at least 10 wt %, at least 15 wt %, at least 20 wt %, at least 30 wt %, at least 40 wt %, at least 50 wt %, at least 60 wt %, at least 70 wt %, or more, based on the total weight of the hydrocarbon-containing feed. In other embodiments, the hydrocarbon-containing feed can include, but is not limited to, one or more $C_2$-$C_5$ alkanes at a total concentration of at least 10 wt %, at least 15 wt %, at least 20 wt %, at least 30 wt %, at least 40 wt %, at least 50 wt %, at least 60 wt %, at least 70 wt %, or more, based on the total weight of the hydrocarbon-containing feed minus any water that may be present therein. In some embodiments, the hydrocarbon-containing feed can include one or more $C_2$-$C_4$ alkanes at a total concentration of at least 10 wt %, based on the total weight of the hydrocarbon-containing feed. In other embodiments, the hydrocarbon-containing feed can include ethane at a concentration of at least 10 wt %, based on the total weight of the hydrocarbon-containing feed stream.

The plastic material can be, or can include, but is not limited to, polyethylene terephthalate (PETE or PET), polyethylene (PE), polypropylene (PP), polyvinyl chloride (PVC), polyvinylidene chloride (PVDC), polystyrene (PS), polycarbonate (PC), polylactic acid (PLA), acrylic (PMMA), acetal (polyoxymethylene, POM), acrylonitrile-butadiene-styrene (ABS), fiberglass, nylon (polyamides, PA), polyester (PES) rayon, polyoxybenzylmethylenglycolanhydride (bakelite), polyurethane (PU), polyepoxide (epoxy), or any mixture thereof. The rubber can be or can include natural rubber, synthetic rubber, or a mixture thereof. The biogas can be produced via anaerobic digestion, e.g., the biogas produced during the anaerobic digestion of sewage. The biobased oil can be or can include oils that can degrade biologically over time. The biobased oil can be degraded via processes of bacterial decomposition and/or by the enzymatic biodegradation of other living organisms such as yeast, protozoans, and/or fungi. Biobased oils can be derived from vegetable oils, e.g., rapeseed oil, castor oil, palm oil, soybean oil, sunflower oil, corn oil, hemp oil, or chemically synthesized esters. The biomass can be or can include, but is not limited to, wood, agricultural residues such as straw, stover, cane trash, and green agricultural wastes, agro-industrial wastes such as sugarcane bagasse and rice husk, animal wastes such as cow manure and poultry litter, industrial waste such as black liquor from paper manufacturing, sewage, municipal solid waste, food processing waste, or any mixture thereof.

If the hydrocarbon-containing feed includes material that is solid at room temperature, e.g., plastic material, biomass, coal, rubber, etc., the solid material can be reduced to any desired particle size via well-known processes. For example, if the hydrocarbon-containing feed includes solid material, the solid material can be ground, crushed, pulverized, other otherwise reduced into particles that have any desired average particle size. In some examples, the solid matter can be reduced to an average particle size that can be submicron or from about 1 µm, about 10 µm or about 50 µm to about 100 µm, about 150 µm, or about 200 µm. For example, the average particle size of the solid material can range from about 75 µm to about 475 µm, from about 125 µm to about 425 µm, or about 175 µm to about 375 µm.

In some embodiments, the hydrocarbon-containing feed can include one or more crude oils or a fraction thereof and one or more plastic materials. In some embodiments, the hydrocarbon-containing feed can include petroleum and one or more plastic materials and the one or more plastic materials can be present in an amount in a range of from 1 wt %, 3 wt %, 5 wt %, 7 wt %, 10 wt %, or 15 wt % to 20 wt %, 25 wt %, 30 wt %, 35 wt %, 40 wt %, or 45 wt %, based on the total weight of the hydrocarbon-containing feed.

The petroleum, e.g., crude oil or fraction thereof, can act as a solvent for the plastic material and cause at least a portion of the plastic material to dissolve in the crude oil or fraction thereof. In some embodiments, at least 30 wt %, at least 40 wt %, at least 50 wt %, at least 60 wt %, at least 70 wt %, at least 80 wt %, at least 90 wt %, or even 100 wt % of the plastic material mixed with the crude oil or fraction thereof can be solubilized in the crude oil or fraction thereof. As such, in some embodiments, when the hydrocarbon-containing feed includes one or more plastic materials, the hydrocarbon-containing feed can be in the form of a solution in which the plastic material is homogeneously dispersed in the crude oil or fraction thereof.

The particles that can be used in the process for converting the hydrocarbon-containing feed by pyrolysis and gasification/combustion can be or can include, but are not limited to, silica, alumina, titania, zirconia, magnesia, pumice, ash, clay, diatomaceous earth, bauxite, spent fluidized catalytic cracker catalyst, or any mixture or combination thereof. In some embodiments, the particles can be or can include a core and at least one transition metal element and/or at least one oxidized transition metal element disposed on and/or in the core. In some embodiments, the core can be or can include, but is not limited to, silica, alumina, titania, zirconia, magnesia, pumice, ash, clay, diatomaceous earth, bauxite, spent fluidized catalytic cracker catalyst, or any mixture or combination thereof. Preferred support materials can be or can include, but are not limited to, $Al_2O_3$, $ZrO_2$, $SiO_2$, and combinations thereof, more preferably, $SiO_2$, $Al_2O_3$, or $SiO_2/Al_2O_3$.

In some embodiments, the transition metal element and/or the oxide thereof can be disposed on and/or within, e.g., within pores, of the core. In some embodiments, the transition metal element and/or the oxide thereof can form a surface layer on the core. The surface layer on the core can be continues or discontinuous. The core and/or the particles that include the at least one transition metal element and/or at least one oxidized transition metal element disposed on and/or in the core can have an average size in a range from 10 micrometers (μm), 15 μm, 25 μm, 50 μm, or 75 μm to 150 μm, 200 μm, 300 μm, 400 μm. The core and/or the particles that include the at least one transition metal element and/or at least one oxidized transition metal element disposed on and/or in the core can have a surface area in a range from 10 $m^2/g$, 50 $m^2/g$, or 100 $m^2/g$ to 200 $m^2/g$, 500 $m^2/g$, or 700 $m^2/g$.

In some embodiments, the particles can be, can include, or can otherwise be derived from spent fluid catalytic cracker ("FCC") catalyst. As such, a significant and highly advantageous use for spent FCC catalyst has been discovered because the processes disclosed herein can significantly extend the useful life of FCC catalyst in upgrading hydrocarbons long after the FCC catalyst is considered to be spent and no longer useful in the fluid catalytic cracking process.

In some embodiments, the particles can include any oxide of a transition metal element capable of converting at least a portion of any molecular hydrogen to water, e.g., via oxidation, combustion, or other mechanism, within the pyrolysis reaction zone. In some embodiments, the transition metal element can be or can include, but is not limited to, titanium, vanadium, chromium, manganese, iron, cobalt, niobium, nickel, molybdenum, tantalum, tungsten, alloys thereof, and mixtures thereof. In some examples, the transition metal element can be or can include vanadium, nickel, an alloy thereof, or a mixture thereof. The amount of optional transition metal element that can be disposed on and/or at least partially within the particles can be in a range from 500 ppm by weight, 750 ppm by weight, 1,000 ppm by weight, 2,500 ppm by weight, 5,000 ppm by weight, or 1 wt % to 2 wt %, 5 wt %, 10 wt %, 15 wt %, 20 wt %, 30 wt %, 40 wt %, or 50 wt %, based on a total weight of the particles. In some embodiments, the amount of optional transition metal element that can be disposed on and/or at least partially within the particles can be at least 1 wt %, at least 2.5 wt %, at least 3 wt %, at least 3.5 wt %, at least 4 wt %, at least 4.5 wt %, at least 5 wt %, or at least 10 wt % up to 15 wt %, 20 wt %, 30 wt %, 40 wt %, or 50 wt %.

Process for Upgrading the Hydrocarbon-Containing Feed Stream

The process for converting a hydrocarbon-containing feed stream by pyrolysis can include feeding the hydrocarbon-containing feed stream that can include $C_{2+}$ hydrocarbons and a first particle stream that can included particles having a pyrolysis temperature into a pyrolysis zone. The hydrocarbon-containing feed stream can be contacted with the particles in the pyrolysis zone to under pyrolysis conditions to effect pyrolysis of at least a portion of the $C_{2+}$ hydrocarbons to produce a pyrolysis zone effluent that can include olefins and the particles. Coke can be formed on the surface of the particles. In some embodiments, the hydrocarbon-containing feed can include water. In other embodiments, the process can also include optionally feeding a steam stream into the pyrolysis zone in addition to the hydrocarbon-containing feed and the heated particles.

In some embodiments, a raw feed that can include $C_{2+}$ hydrocarbons can be heated, e.g., to a temperature in a range of from 200° C., 250° C., 300° C., or 325° C. to 400° C., 450° C., 500° C., 600° C., or 700° C., and introduced into a hydrocarbon feed separation stage to produce a heated raw feed. The heated raw feed can be separated to obtain a vapor fraction and a liquid fraction. In some embodiments, at least a portion of the vapor fraction can be fed as at least a portion of the hydrocarbon-containing feed into the pyrolysis zone. In other embodiments, at least a portion of the liquid fraction can be fed as at least a portion of the hydrocarbon-containing feed into the pyrolysis zone. In still other embodiments, at least a portion of the vapor fraction and at least a portion of the liquid fraction can be fed as at least a portion of the hydrocarbon-containing feed into the pyrolysis zone. In some embodiments, when both the vapor fraction and the liquid fraction are fed into the pyrolysis zone, the vapor fraction can be fed into a first pyrolysis feed inlet and the liquid fraction can be fed into a second pyrolysis feed inlet, where the second pyrolysis feed inlet can be downstream of the first pyrolysis feed inlet. It should be understood that when the hydrocarbon-containing feed includes hydrocarbons in the liquid phase, at least a portion and in some embodiments all of the liquid phase hydrocarbons can be vaporized within the pyrolysis zone essentially immediately upon introduction of the hydrocarbon-containing feed into the pyrolysis zone.

The first pyrolysis zone can be located in any suitable reactor or other process environment capable of operating under the pyrolysis process conditions. In some embodiments, the first pyrolysis zone can be located in short contact time fluid bed. In some embodiments, the first pyrolysis zone can be located in a downflow reactor, an upflow reactor, a counter-current flow reactor, or vortex reactor. In a preferred embodiment, the first pyrolysis zone can be located in a downflow reactor.

The pyrolysis temperature of the particles can be in a range of from 750° C., 800° C., 850° C., 900° C., or 950° C. to 1,050° C., 1,100° C., 1,200° C., 1,300° C., 1,400° C., or 1,500° C. In some embodiments, the pyrolysis temperature of the particles can be at least 800° C., at least 820° C., at least 840° C., at least 850° C., at least 875° C., at least 900° C., at least 950° C., or at least 975° C. to 1,000° C., 1,050° C., 1,100° C., 1,200° C., 1,300° C., or 1,400° C. In some embodiments, the pyrolysis zone effluent can be at a temperature of 800° C., 850° C., 900° C., 925° C., or 950° C. to 975° C., 1,000° C., 1050° C., 1,100° C., or 1,150° C.

The hydrocarbon-containing feed can be contacted with an amount of the particles within the pyrolysis zone sufficient to effect a desired level or degree of pyrolysis of the hydrocarbon-containing feed. In some embodiments, a weight ratio of the particles to the hydrocarbon-containing feed when contacted within the pyrolysis zone can be 5, 10, 12, 15, or 20 to 25, 30, 35, 40, 45, 50, 55, or 60. In some embodiments, the optional steam stream can be introduced or otherwise fed into the pyrolysis zone in an amount sufficient to provide a weight ratio of the steam to the hydrocarbon-containing feed of greater than zero to 2 or 4 or 6, e.g., 0.01, 0.05, 0.1, 0.5, or 0.7 to 1, 2, 3, 4, 5, or 6.

The hydrocarbon-containing feed can contact the particles within the pyrolysis zone under a vacuum, at atmospheric pressure, or at a pressure greater than atmospheric pressure. In some embodiments, the hydrocarbon-containing feed can contact the particles within the pyrolysis zone under an absolute pressure of 100 kPa, 500 kPa, 1,000 kPa, or 1,500 kPa to 3,000 kPa, 4,000 kPa, 5,000 kPa, 6,000 kPa, or 7,000 kPa. In other embodiments, the hydrocarbon-containing feed can contact the particles within the pyrolysis zone under an absolute pressure of 100 kPa, 150 kPa, 200 kPa, 250 kPa, 300 kPa, or 400 kPa to 450 kPa, 500 kPa, 550 kPa, 600 kPa, 650 kPa, 700 kPa, 750 kPa, 800 kPa, or 840 kPa. In still other embodiments, the hydrocarbon-containing feed can contact the particles within the pyrolysis zone under an absolute pressure of less than 800 kPa, less than 700 kPa, less than 600 kPa, less than 500 kPa, less than 450 kPa, less than 400 kPa, less than 350 kPa, less than 300 kPa, less than 250 kPa, less than 200 kPa, or less than 150 kPa.

In some embodiments, the velocity of the gaseous components within the pyrolysis zone can be in a range of 9 m/s, 20 m/s, 50 m/s, or 75 m/s to 100 m/s, 115 m/s, 130 m/s, 155 m/s, or 175 m/s. In some embodiments, the velocity of the particles within the pyrolysis zone can be up to 3 m/s, 5 m/s, 7 m/s, 10 m/s, 12, m/s, or 15 m/s. In some embodiments, the velocity of the gaseous components within the pyrolysis zone can be at least 15%, at least 20%, at least 25%, at least 30%, at least 35%, at least 40%, at least 45%, or at least 50% greater than a velocity of the particles within the pyrolysis zone.

The hydrocarbon-containing feed can contact the particles within the pyrolysis zone for a residence time of 1 millisecond (ms), 5 ms, 10 ms, 25 ms, 50 ms, 75 ms, or 100 ms to 300 ms, 500 ms, 750 ms, 1,000 ms, 1,250 ms, 1,500 ms, 1,750 ms, or 2,000 ms. In some embodiments, the hydrocarbon-containing feed can contact the particles within the pyrolysis zone for a residence time of 10 ms to 700 ms, 10 ms to 500 ms, 10 ms to 100 ms, 20 ms to 200 ms, 30 ms to 225 ms, 50 ms to 250 ms, 125 ms to 500 ms, 200 ms to 600 ms, or 20 ms to 140 ms. In other embodiments, the hydrocarbon-containing feed can contact the particles within the pyrolysis zone for a residence time of less than 1,000 ms, less than 800 ms, less than 600 ms, less than 400 ms, less than 300 ms, less than 200 ms, less than 150 ms, or less than 100 ms.

As noted above, during contact of the hydrocarbon-containing feed with the particles in the pyrolysis zone, coke can be formed on the surface of the particles. For example, when hydrocarbon-containing feed includes non-volatile components at least a portion of the non-volatile components can deposit, condense, adhere, or otherwise become disposed on the surface of the particles and/or at least partially within the particles, e.g., within pores of the particles, in the form of coke. In some embodiments, the particles in the first pyrolysis zone effluent can include 1 wt %, 3 wt %, 5 wt %, 7 wt %, 10 wt %, or 15 wt % to 20 wt %, 25 wt %, 30 wt %, 35 wt %, 40 wt %, 45 wt %, or 50 wt % of coke, based on a total weight of the particles in the pyrolysis zone effluent.

A pyrolysis zone effluent that can include hydrocarbons, e.g., olefins, and the particles that can include the coke formed thereon can be obtained from the pyrolysis zone. The pyrolysis zone effluent can be fed from the pyrolysis zone into one or more first separation stages configured or adapted to receive the pyrolysis zone effluent and separate a first gaseous stream rich in the hydrocarbons, e.g., olefins, and a second particle stream rich in the particles. The first separation stage can be configured or adapted to discharge the first gaseous stream and the second particle stream therefrom.

In some embodiments, at least a portion of the particles in the pyrolysis zone effluent can optionally be stripped by contacting the particles in the pyrolysis zone effluent with a stripping medium within the first separation stage. For example, the pyrolysis zone effluent can be fed from the pyrolysis zone into the first separation stage, which can be configured or adapted to contact the pyrolysis zone effluent or at least a portion of the particles in the pyrolysis zone effluent with a stripping medium, e.g., a first steam stream, and separate the pyrolysis zone effluent to obtain the first gaseous stream rich in the olefins and rich in the optional stripping medium and the second particle stream rich in the particles. As such, in some embodiments, the first separation stage can also be referred to as a stripping vessel. In some embodiments, a residence time of the particles in the pyrolysis zone effluent separated within the first separation stage from the pyrolysis zone effluent can be in a range from 30 seconds, 1 minute, 3 minutes, 5 minutes, or 10 minutes to 15 minutes, 17 minutes, 20 minutes, 25 minutes, or longer before being discharged therefrom as the second particle stream rich in particles. In some embodiments, the optional stripping medium can fed into the first separation stage at a weight ratio of the stripping medium to the pyrolysis zone effluent fed into the first separation stage in a range from 1:1,000, 2:1,000, or 2.5:1,000, or 3:1,000 to 4:1,000, 6:1,000, 8:1,000, or 10:1,000.

In some embodiments, the first separation stage can include an inertial separator configured to separate a majority of the particles from the hydrocarbons to produce the first gaseous stream rich in hydrocarbons and the second particle stream rich in the particles. Inertial separators can be configured or adapted to concentrate or collect the particles by changing a direction of motion of the first pyrolysis zone effluent such that the particle trajectories cross over the hydrocarbon gas streamlines and the particles are either concentrated into a small part of the gas flow or are separated by impingement onto a surface. In some embodiments, a suitable inertial separator can include a cyclone. Illustrative cyclones can include, but are not limited to, those disclosed in U.S. Pat. Nos. 7,090,081; 7,309,383; and 9,358, 516.

In some embodiments, a residence time within the first separation stage of the hydrocarbons separated from the pyrolysis zone effluent can be less than 1,000 ms, less than 750 ms, less than 500 ms, less than 250 ms, less than 100 ms, less than 75 ms, less than 50 ms, or less than 25 ms. In some embodiments, a residence time within the first separation stage of the hydrocarbons separated from the pyrolysis zone effluent can be in a range from 2 ms, 4 ms, 6 ms, or 8 ms to 10 ms, 12 ms, 14 ms, 16 ms, 18 ms, or 20 ms before being discharged therefrom as the first gaseous stream. In some embodiments, the residence time within the first separation stage of the hydrocarbons separated from the pyrolysis zone effluent can be less than 20 ms, less than 15 ms, less than 10 ms, less than 7 ms, less than 5 ms, or less than 3 ms before being discharged therefrom as the first gaseous stream. The first gaseous stream, upon being discharged from the first separation stage, can be free or substantially free of any particles. In some embodiments, the first gaseous stream discharged from the first separation stage can include less than 25 wt %, less than 20 wt %, less than 15 wt %, less than 12 wt %, less than 10 wt %, less than 8 wt %, less than 6 wt %, less than 5 wt %, less than 3 wt %, or less than 1 wt % of the particles present in the pyrolysis zone effluent.

In some embodiments, a residence time of the hydrocarbons in the first gaseous stream separated from the pyrolysis zone effluent spanning from the initial introduction of the hydrocarbon-containing feed and the heated particles into the pyrolysis zone to the recovery of the first gaseous stream rich in the olefins from the first separation stage can be 5 ms, 10 ms, 25 ms, 50 ms, 75 ms, or 100 ms to 300 ms, 500 ms, 750 ms, 1,000 ms, 1,250 ms, 1,500 ms, 1,750 ms, or 2,000 ms. In other embodiments, the residence time of the hydrocarbons in the first gaseous stream separated from the pyrolysis zone effluent spanning from the initial introduction of the hydrocarbon-containing feed and the heated particles into the pyrolysis zone to the recovery of the first gaseous stream rich in the olefins from the first separation stage can be less than 1,500 ms, less than 1,250 ms, less than 1,000 ms, less than 800 ms, less than 600 ms, less than 400 ms, less than 300 ms, less than 200 ms, less than 150 ms, or less than 100 ms.

At least a portion of the second particle stream, an oxidant stream, optionally a second steam stream, optionally a fuel stream, and/or optionally a diluent stream can be fed into a gasification/combustion zone. The second particle stream, the oxidant stream, the optional second steam stream, the optional fuel stream, and/or the optional diluent stream can be contacted within the gasification/combustion zone to effect gasification and/or combustion of at least a portion of the coke disposed on the surface of the particles to produce a gasification/combustion zone effluent that can include heated and regenerated particles and a gasification/combustion gas mixture. The reactions that can occur within the gasification/combustion zone can include, but are not limited to, combustion ($C+O_2 \rightarrow CO_2$; $2H_2+O_2 \rightarrow 2H_2O$), gasification ($C+H_2O \rightarrow CO+H_2$; $C+CO_2 \rightarrow 2CO$); and/or water gas shift reaction ($CO+H_2O \leftrightarrow CO_2+H_2$). As such, in some embodiments the gasification/combustion zone can be configured to produce primarily a gasification/combustion gas mixture that can include a synthesis gas that can include molecular hydrogen ($H_2$), carbon monoxide (CO), and carbon dioxide ($CO_2$). In other embodiments, the gasification/combustion zone can be configured to produce primarily a gasification/combustion gas mixture that can include a flue gas that can include carbon dioxide ($CO_2$) and water ($H_2O$) or molecular nitrogen ($N_2$), carbon dioxide ($CO_2$) and water ($H_2O$).

The oxidant stream can be or can include molecular oxygen such as air, oxygen enriched air, oxygen depleted air, or any mixture thereof. In some embodiments, the oxidant stream can be a molecular oxygen containing gas that can have a relatively high molecular nitrogen content. For example, the oxidant stream can include molecular oxygen and molecular nitrogen, with the molecular nitrogen at a concentration of $\geq 15$ vol %, $\geq 25$ vol %, $\geq 40$ vol %, $\geq 60$ vol %, $\geq 70$ vol %, $\geq 80$ vol %, or $\geq 85$ vol %, based on the total volume of the oxidant stream. In some embodiments, the oxidant stream can be a molecular oxygen containing gas that can have relatively a low nitrogen content, such as oxygen from an air separation unit. For example, the oxidant stream can include $\geq 40$ vol %, $\geq 50$ vol %, $\geq 60$ vol %, $\geq 70$ vol %, $\geq 80$ vol %, $\geq 90$ vol %, $\geq 95$ vol %, $\geq 98$ vol %, or more of molecular oxygen and $<60$ vol %, $<50$ vol %, $<40$ vol %, $<30$ vol %, $<20$ vol %, $<10$ vol %, $<5$ vol %, $<2$ vol %, or less of molecular nitrogen, based on the total volume of the oxidant stream. In some embodiments, the oxidant stream can include molecular oxygen at a concentration of $\geq 85$ vol %, $\geq 90$ vol %, $\geq 95$ vol %, 97 vol %, 98 vol %, 99 vol %, or 99.5 vol % and molecular nitrogen at a concentration of $\leq 15$ vol %, $\leq 10$ vol % $\leq 5$ vol %, $\leq 3$ vol %, or $\leq 1$ vol %, based on the total volume of the oxidant stream.

The fuel can be or can include any combustible source of material capable of combusting in the presence of the oxidant stream within the gasification/combustion zone. Suitable fuels can be or can include, but are not limited to, molecular hydrogen, methane, ethane, propane, butane, natural gas, naphtha, gas oil, fuel oil, quench oil, fuel gas such as a mixture of one or more $C_1$-$C_5$ hydrocarbons, or any mixture thereof. In some embodiments, the fuel stream can be fed into the gasification/combustion zone and a first portion of the fuel stream can be combusted within the gasification/combustion zone and a second portion of the fuel stream can be converted into molecular hydrogen and carbon monoxide. The diluent can be any essentially inert gas such as carbon dioxide, molecular nitrogen, or a mixture thereof.

The gasification/combustion zone can be operated at a temperature of 1,000° C., 1,050° C., 1,100° C., 1,150° C., 1,200° C., 1,250° C., or 1,300° C. to 1,350° C., 1,400° C., 1,450° C., or 1,500° C. Operating the gasification/combustion zone at such an elevated temperature can produce heated and regenerated particles having a sufficient amount of heat that can be utilized within the pyrolysis zone to effect the pyrolysis of the hydrocarbon-containing feed. The gasification/combustion zone can be operated at a pressure of 100 kPa-absolute, 200 kPa-absolute, 300 kPa-absolute, 400 kPa-absolute, or 500 kPa-absolute to 700 kPa-absolute, 800 kPa-absolute, 900 kPa-absolute, or 1,000 kPa-absolute. In some embodiments, the gasification/combustion zone can be operated at a temperature of at least 1,000° C., e.g., 1,200° C. to 1,500° C., and at a pressure of <800 kPa-absolute. In other embodiments, the gasification/combustion zone can be operated at a temperature of at least 1,000° C., e.g., 1,200° C. to 1,500° C., and at a pressure of $\geq 800$ kPa-absolute, such as 800 kPa-absolute to 7,000 kPa-absolute.

In some embodiments, the amount of oxidant introduced into the gasification/combustion zone can be reduced or limited to a substoichiometric amount that would be needed for complete combustion of all the coke disposed on the particles and, if present, all of the hydrocarbon fuel introduced into the gasification/combustion zone. The amount of oxidant introduced into the gasification/combustion zone can be sufficient to combust a sufficient amount of the coke and, if present, optionally combust a sufficient amount of the fuel to provide heat for the gasification/combustion zone and at least a portion of the heat within the pyrolysis zone via the heated and regenerated particles recycled thereto. In some embodiments, the amount of oxidant introduced into the gasification zone can be 30% to 90% or 50% to 70% of the amount of oxidant that would be required for complete combustion of all the coke formed on the surface of the particles and, if present, all of the fuel introduced into the gasification/combustion zone.

In some embodiments, when the second particle stream rich in particles includes coke disposed on and/or at least partially in the particles, at least a portion of the coke can be gasified in the gasification/combustion zone to produce the gasification/combustion gas mixture that can include molecular hydrogen, carbon monoxide, and carbon dioxide. In other embodiments, when the second particle stream rich in particles includes coke disposed on and/or at least partially in the particles, at least a portion of the coke can be combusted within the gasification/combustion zone to produce the gasification/combustion gas mixture that can include a flue gas that can include molecular nitrogen, carbon dioxide, and water. In still other embodiments, when the second particle stream rich in particles includes coke disposed on and/or at least partially in the particles, at least a portion of the coke can be gasified and at least a portion of the coke can be combusted within the gasification/combustion zone to produce the gasification/combustion gas mixture.

The heated and regenerated particles in the gasification/combustion zone effluent can include less coke as compared to the particles in the second particle stream rich in the particles or can be free of any coke. In some embodiments, the particles in the heated and regenerated particles in the gasification/combustion zone effluent can include less than 5 wt %, less than 4 wt %, less than 3 wt %, less than 2 wt %, less than 1 wt %, less than 0.5 wt %, or less than 0.1 wt % of coke.

In some embodiments, when the particles include the oxide of a transition metal element capable of oxidizing molecular hydrogen within the pyrolysis zone, at least a portion of the transition metal element disposed on and/or in the particles in the pyrolysis zone effluent can be at a reduced state as compared to the transition metal element in the particles fed into the pyrolysis zone. Without wishing to be bound by theory, it is believed that when the particles include the optional oxide of the transition metal element capable of oxidizing molecular hydrogen within the pyrolysis zone, the oxide of the transition metal element can do so via one or more processes or mechanisms. Regardless of the overall mechanism, the oxidized transition metal element can facilitate the conversion of molecular hydrogen to water and in doing so the oxidation state of the oxide of the transition metal element can be reduced. For example, if the transition metal element is vanadium, the oxide of vanadium on the fluidized particles fed into the pyrolysis reaction zone can be at an oxidation state of +5 (for example) and at least a portion of the oxide of vanadium on the fluidized particles in the pyrolysis effluent can be at an oxidation state of +4, +3, or +2. Without wishing to be bound by theory, it is also believed that one or more of the oxides of one or more transition metal elements may be capable of being reduced from an oxidized state all the way to the metallic state.

Additionally, the oxide of the transition metal element, if present, can favor the conversion, e.g., oxidation and/or combustion, of hydrogen over the oxidation and/or combustion of hydrocarbons, e.g., olefins, in the pyrolysis zone. In some embodiments, the oxide of the transition metal element can favor the conversion of hydrogen over the conversion of hydrocarbons at a rate of 2:1, 3:1, 4:1, 5:1, 6:1, or 7:1 to 8:1, 9:1, 10:1, or 11:1.

The gasification/combustion zone effluent can be separated into a third particle stream that can be rich in the heated and regenerated particles and a second gaseous stream rich in the gasification/combustion gas mixture. In some embodiments, the gasification/combustion zone effluent can be introduced or otherwise fed into a second separation stage that can be configured to separate at least a majority of the heated and regenerated particles from the gaseous components to produce the second gaseous stream rich in the gasification/combustion gas mixture and the third particle stream rich in the heated and regenerated particles. In some embodiments, the second separation stage can be or can include one or more inertial separators similar to or the same as those described above with regard to the first separation stage.

At least a portion of the third particle stream rich in the regenerated particles can be recycled or otherwise fed into the pyrolysis zone as at least a portion of the first particle stream. In some embodiments, a portion of the second gaseous stream rich in the gasification/combustion gas mixture can be fed as the diluent stream into the gasification/combustion zone.

Returning to the first gaseous steam rich in the hydrocarbons, in some embodiments, at least a portion of the first gaseous stream can be fed into an oligomerization zone and contacted therein with oligomerization catalyst. In some embodiments, at least a portion of the olefins, e.g., ethylene, propylene, and/or other $C_{5-}$ or $C_{6-}$ olefins, upon contact with the oligomerization catalyst can react to produce an oligomerization zone effluent. In some embodiments, at least a majority of the olefins, e.g., ethylene, propylene, and/or other $C_{5-}$ or $C_{6-}$ olefins, upon contact with the oligomerization catalyst can react to produce an oligomerization zone effluent. The oligomerization zone effluent can include higher molecular weight compounds derived from the olefins. Any convenient type of oligomerization catalyst and/or conditions and/or catalyst bed configuration(s) can be used. In some embodiments, the oligomerization catalyst can be in a fluidized bed within the oligomerization zone. In other embodiments, the oligomerization catalyst can be in a fixed catalyst bed.

In some embodiments, the oligomerization can selectively be performed on olefins of a desired size by performing separations prior to oligomerization. For example, a cooling chamber or another type of separator can be used to separate $C_{4+}$ olefins from $C_2$ and $C_3$ olefins in the first gaseous stream. The fraction containing the $C_2$ and $C_3$ olefins can be exposed to the oligomerization catalyst under oligomerization conditions. Alternatively, it could be desirable to perform separations to generate a fraction containing $C_2$ olefins for oligomerization. In a preferred embodiment, a light product fraction that can include $C_{5-}$ or $C_{6-}$ light hydrocarbons (including olefins) without any separation of $CO_2$ can be contacted with the oligomerization catalyst. In such embodiment, the olefins in the light product fraction can be upgraded without expensive separation(s) of $CO_2$ from the light hydrocarbons. The remaining hydrocarbon gases after oligomerization can be substantially less expensive to separate from the $CO_2$, if desired, or the remaining light hydrocarbon gases can be used as a fuel, e.g., as the optional fuel that can be introduced into the gasification/combustion zone. In this embodiment, the $CO_2$ content of the fuel gas can be admixed with the second gaseous stream rich in the gasification/combustion gas mixture obtained from the gasification/combustion zone effluent and $CO_2$ recovery can be achieved in one process instead of two separate processes.

The oligomerization can be performed by any convenient process. The temperature within the oligomerization zone can be in the range of from 215° C., 300° C., 350° C., 400° C., 450° C. to 500° C., 525° C., 540° C., 600° C., 650° C., or 700° C. The pressure within the oligomerization zone can be in the range of from 50 kPa-absolute, 100 kPa-absolute, 250 kPa-absolute, 500 kPa-absolute, 750 kPa-absolute, or 1,000 kPa-absolute to 1,250 kPa-absolute, 1,500 kPa-absolute, 2,000 kPa-absolute, 2,500 kPa-absolute, or 3,000 kPa-absolute. In some embodiments, the oligomerization catalyst can be a zeolite. Suitable zeolites can be or can include, but are not limited to, ZSM-5, ZSM-11, ZSM-12, ZSM-22, ZSM-23, ZSM-35, ZSM-48, or any mixture thereof. In some embodiments, the oligomerization catalyst can be a ZSM-5, a phosphorous-modified ZSM-5, Ni-doped ZSM-5, or any mixture thereof.

In some embodiments, the oligomerization catalyst can include a zeolite that can have an alpha value of 1, 2, 5, 10, 15, 20, or 25 to 40, 50, 60, 70, 80, 90, or 100. Alpha value is a measure of the acid activity of a zeolite catalyst as compared with a standard silica-alumina catalyst. The alpha value refers to a measure of the cracking activity of a catalyst and is described in U.S. Pat. No. 3,354,078 and in the Journal of Catalysis, Vol. 4, p. 527 (1965); Vol. 6, p. 278 (1966) and the Journal of Catalysis, Vol. 61, p. 395 (1980). The alpha value can be measured at a temperature of 538° C. and a variable flow rate as described in the Journal of Catalysis, Vol. 61, p. 395 (1980). In some embodiments, the zeolite can be bound with a suitable inorganic oxide, such as silica, alumina, etc. to provide a zeolite concentration of 5 wt % to 95 wt %.

By using an oligomerization process that is suitable for use with the first gaseous stream rich in the olefins, the olefins from the pyrolysis effluent can be converted to heavier liquid products (i.e., gasoline and/or diesel boiling range products) without requiring prior separation of $CO_2$ and/or other non-olefin compounds from the first gaseous stream. In some embodiments the oligomerization conditions can include conditions similar to or the same as those in the Mobil Olefins to Gasoline (MOG) Mobil Olefins to Gasoline/Distillate (MOGD), and/or the Mobil Olefins to Gasoline/Distillate/Lubes (MOGDL) processes. Illustrative oligomerization catalysts, process conditions, systems, etc. can include, but are not limited to, those described in U.S. Pat. Nos. 3,960,978; 4,021,502; 4,150,062; 4,211,640; 4,227,992; 4,422,185; 4,456,781; 4,483,760; 5,013,329; 5,043,499; and 5,583,276.

In some embodiments, heat can be removed from the oligomerization zone via one or more catalyst coolers. For example, a portion of the oligomerization catalyst can be removed or otherwise obtained from the oligomerization zone, passed through an indirect heat exchange stage, and fed back into the oligomerization zone. The indirect heat exchange stage can transfer heat from the catalyst to reduce a temperature of the oligomerization catalyst and, thereby reducing the temperature within the oligomerization zone. In other embodiments, the oligomerization zone can include an embedded heat exchanger located therein such that heat can be transferred away from the oligomerization zone through the embedded heat exchanger to reduce the temperature inside the oligomerization zone. For example, one or more tube bundles configured to flow a cooling medium therethrough can be submerged or embedded within the oligomerization catalyst bed.

When the oligomerization catalyst activity decreases below a desired level due to the accumulation of coke, a portion of the oligomerization catalyst can be recovered or otherwise obtained from the oligomerization zone and introduced along with an oxidant and, optionally, a fuel, into a regeneration zone. In some embodiments, at least a portion of the coke can be combusted within the regeneration zone to produce a regeneration zone effluent. A regenerated oligomerization catalyst and a third gaseous stream can be separated or otherwise obtained from the regeneration zone effluent. At least a portion of the regenerated oligomerization catalyst can be fed back into the oligomerization zone. In some embodiments, a portion of the catalyst can be removed from the regeneration zone or any other location and make-up catalyst can be fed into the oligomerization zone or any other location to maintain a desired catalyst inventory within the oligomerization zone.

It should also be noted that, in some embodiments, the first gaseous stream rich in the olefins can include catalyst fines or fine particles when introduced into the oligomerization zone. As such, in some embodiments, essentially all of the fine particles do not need to be removed from the first gaseous stream before feeding the first gaseous stream into the oligomerization zone. Rather, the oligomerization zone can receive the catalyst fines and process them along with the oligomerization catalyst. In some embodiments, the first gaseous stream can include fine particles at a concentration in a range of from 0.1 wt %, 0.5 wt %, 1 wt %, 1.5 wt %, or 3 wt % to 3 wt %, 5 wt %, 7 wt %, 10 wt %, or more, based on a total weight of the first gaseous stream when fed into the oligomerization zone. As such, in some embodiments, when the first gaseous steam includes fine particles from the first particle stream, removing or otherwise purging a portion of the catalyst from the regeneration zone can maintain a desired concentration of fine particles within the oligomerization zone.

In some embodiments, the oligomerization zone effluent can be fed directly from the oligomerization zone into a fourth separation stage to separate at least one of a light gas stream that can include molecular hydrogen and one or more $C_1$-$C_4$ hydrocarbons and at least one $C_{5+}$ hydrocarbon stream. In some embodiments, the at least one $C_{5+}$ hydrocarbon stream can include a gasoline stream and/or a distillate stream. In some embodiments, the $C_{5+}$ hydrocarbon stream can include sulfur at a concentration of no greater than 10 ppm by weight, based on the total weight of the $C_{5+}$ hydrocarbon stream, and the light gas stream can include hydrogen sulfide. Recovery of a $C_{5+}$ hydrocarbon stream that includes no greater than 10 ppm by weight of sulfur, based on the total weight of the $C_{5+}$ hydrocarbon stream, without the need for a separate hydrodesulfurization stage provides a significant technical advantage that is enabled by the relatively high molecular hydrogen environment within the oligomerization zone. The oligomerization zone can have a sufficient amount of molecular hydrogen and/or sufficient severity to provide sufficient hydrogen transfer rates therein to enable the production of a $C_{5+}$ hydrocarbon stream that includes no greater than 10 ppm by weight of sulfur, based on the total weight of the $C_{5+}$ hydrocarbon stream.

In other embodiments, the at least one $C_{5+}$ hydrocarbon stream can include sulfur at a concentration of at least 11 ppm by weight, based on the total weight of the $C_{5+}$ hydrocarbon stream. In this embodiment, the $C_{5+}$ hydrocarbon stream and molecular hydrogen can be fed into a hydrodesulfurization stage or blended with lower sulfur components to produce a product meeting the desired sulfur specification. The $C_{5+}$ hydrocarbon stream and molecular hydrogen can be contacted in the presence of a suitable hydroprocessing catalyst under hydrodesulfurization conditions to produce a hydrodesulfurization effluent rich in hydrogen sulfide. The hydrogen sulfide can then be separated or otherwise removed from the hydrodesulfurization effluent to obtain a hydrogen sulfide lean $C_{5+}$ hydrocarbon product stream that can include no greater than 10 ppm by weight of sulfur, based on the total weight of the hydrogen sulfide lean $C_{5+}$ hydrocarbon product stream.

In some embodiments, a gasoline stream that can include, at least predominantly, $C_5$-$C_{12}$ hydrocarbons can be obtained from the oligomerization zone effluent. In one embodiment, the gasoline stream can include, at least predominantly, C5-$C_{12}$ hydrocarbons and can have a boiling range of from 37° C. to 165° C. In another embodiment, the gasoline stream can also meet ASTM D4814-20a. In some embodiments, a distillate stream that can include, at least predominantly, $C_{10}$-$C_{25}$ hydrocarbons can be separated or otherwise obtained from the oligomerization zone effluent. In one embodiment, distillate stream can include, at least predominately $C_{10}$-$C_{18}$ hydrocarbons and can have a boiling range of from about 165° C. to 593° C. Examples of distillates can include, but are not limited to, naphtha, jet fuel, diesel, kerosene, aviation gas, fuel oil, and blends thereof.

Returning to the second gaseous stream, in some embodiments, the second gaseous stream can include a syngas that can include molecular hydrogen and carbon monoxide. In some embodiments, the second gaseous stream can include molecular hydrogen ($H_2$) at a concentration of from 8 vol %, 10 vol %, or 12 vol % to 20 vol %, 25 vol %, or 28 vol %, carbon monoxide at a concentration of from 10 vol %, 15 vol % or 20 vol % to 25 vol %, 30 vol %, or 35 vol %, and carbon dioxide at a concentration of 3 vol %, 4 vol %, or 5 vol %, based on the total volume of the second gaseous stream. In some embodiments, the second gaseous stream, on a volume basis, can include a greater amount of molecular nitrogen than a combined amount of molecular hydrogen, carbon monoxide, and carbon dioxide.

In some embodiments, heat can be indirectly transferred from the second gaseous stream that can be rich in the gasification/combustion gas mixture to a cooling medium to produce a cooled second gaseous stream that can include water in the liquid phase. In some embodiments, the cooled second gaseous stream can be introduced or otherwise fed into a third separation stage where, at least a portion of the water and, if present, optionally at least a portion of any regenerated particles and/or, if present, optionally at least a portion of any hydrogen sulfide can be separated therefrom to produce a purified second gaseous stream. At least a portion of the purified second gaseous stream can be compressed to produce a compressed second gaseous stream. In some embodiments, a portion of the compressed second gaseous stream can be fed to into the gasification/combustion zone as the optional diluent stream.

In some embodiments, when the oxidant stream includes molecular nitrogen at a concentration of ≥15 vol %, based on the total volume of the oxidant stream, the gasification/combustion zone can be operated under primarily as a gasification zone such that the second gaseous stream includes molecular hydrogen, carbon monoxide, carbon dioxide, and molecular nitrogen. In this embodiment, at least a portion of the second gaseous stream can be reacted with additional steam under shifting conditions to produce a shifted gas stream. The shifted gas stream can include carbon dioxide at a concentration of ≥20 vol %, ≥25 vol %, or 30 vol %, based on the total volume of the shifted gas stream. The shifted gas stream can be separated to provide a carbon dioxide-rich stream and a carbon dioxide-lean gas stream that can include molecular hydrogen and molecular nitrogen. In some embodiments, at least a portion of the carbon dioxide-lean gas stream can be combusted to produce heat. In some embodiments, a fuel can be combined with the carbon dioxide-lean gas stream to produce an adjusted gas stream and at least a portion of the adjusted gas stream can be combusted to produce heat. The fuel can be or can include, but is not limited to, methane, ethane, propane, butane, or a mixture thereof. In this embodiment, a portion of the second gaseous stream can be introduced into the gasification/combustion zone as the diluent stream.

In some embodiments, when the oxidant stream includes molecular nitrogen at a concentration of ≥15 vol %, based on the total volume of the oxidant stream, the gasification/combustion zone can be operated primarily as a gasification zone such that the second gaseous stream includes molecular hydrogen, carbon monoxide, carbon dioxide, and molecular nitrogen. In this embodiment, heat can be indirectly transferred from the second gaseous stream to a cooling medium to produce a cooled second gaseous stream that can include water in the liquid phase. At least a portion of the water and, if present, optionally at least a portion of any regenerated particles and/or, if present, optionally at least a portion of any hydrogen sulfide can be separated from the cooled second gaseous stream to produce a purified second gaseous stream. Any convenient method for removal of hydrogen sulfide can be used. In some examples, the hydrogen sulfide can be removed in an adsorbent stage, such as a Flexsorb® sulfur removal stage. In some embodiments, the sulfur removal stage can be selective for the removal of sulfur, e.g., hydrogen sulfide, while reducing or minimizing removal of carbon dioxide. In some embodiments, the sulfur removal systems and processes disclosed in WO Publication No. 2009/017811. At least a portion of the purified second gaseous stream can be compressed to produce a compressed second gaseous stream. In this embodiment, at least a portion of the compressed second gaseous stream can be reacted with additional steam under shifting conditions to produce a shifted gas stream. In some embodiments, a portion of the compressed second gaseous stream can be introduced into the gasification/combustion zone as at least a portion of the optional diluent stream. The shifted gas stream can be separated to provide a carbon dioxide-rich stream and a carbon dioxide-lean gas stream that can include molecular hydrogen and molecular nitrogen. Any convenient type of carbon dioxide separation can be used, such as cryogenic separation, membrane separation, and/or adsorption (including swing adsorption).

In some embodiments, when the oxidant stream includes molecular oxygen at a concentration of ≥95 vol % and molecular nitrogen at a concentration ≤5 vol %, based on the total volume of the oxidant stream, the gasification/combustion zone can be operated primarily as a combustion zone such that the second gaseous stream includes a flue gas that includes carbon dioxide and water. In this embodiment, heat can be indirectly transferred from the second gaseous stream to a cooling medium to produce a cooled second gaseous stream that can include water. At least a portion of the water can be separated from the cooled second gaseous stream to produce a carbon dioxide-rich stream that includes carbon dioxide at a concentration of 90 vol %, based on the total volume of the carbon dioxide-rich stream. In this embodiment, if the second gaseous stream includes any catalyst fines or fine particles, if the second gaseous steam includes any sulfur dioxide ($SO_2$), and/or if the second gaseous stream includes any nitrogen oxides (NOx), at least a portion of any one or more of the fine particles, sulfur dioxide, and/or nitrogen oxide can optionally be removed or otherwise abated from the second gaseous stream.

If nitrogen oxides are present in the second gaseous stream and it is preferred to remove at least a portion of the nitrogen oxides, the second gaseous stream can be introduced into a DeNOx reactor to remove at least a portion of any nitrogen oxides. The DeNOx reactor can include one or more catalysts that can contact the second gaseous stream in the presence of molecular hydrogen under conditions sufficient to convert at least a portion of any nitrogen oxides to ammonia. In some embodiments, the catalyst can be or can include, but is not limited to, nickel-based sulfided catalysts, copper-based catalysts, and the like. In other embodiments, selective catalytic reduction can be used to convert nitrogen oxides into molecular nitrogen and water. A reductant such as anhydrous ammonia, aqueous ammonia, or a urea solution can be added to the second gaseous stream to drive the reaction toward completion. Suitable catalysts for in the selective catalytic reduction process can be or can include, but are not limited to, one or more oxides of a base metal such as vanadium, molybdenum, and/or tungsten disposed on a support such as titanium oxide, one or more zeolites, one or more precious metals, and the like. Other nitrogen oxide removal processes and systems can also include those disclosed in U.S. Pat. Nos. 3,900,554; 4,104,361; 4,164,546; 4,235,704; and 4,254,616. Processes and systems for removing SOx are well-known and can include those described in U.S. Pat. Nos. 3,873,670; 4,001,375; 4,071,436; 4,059,418; 4,254,616; 5,120,517; 5,741,469; 5,728,358; and WO Publication No. 2009/017811.

In some embodiments, when the oxidant stream includes molecular oxygen at a concentration of ≥95 vol % and molecular nitrogen at a concentration ≤5 vol %, based on the total volume of the oxidant stream, the gasification/combustion zone can be operated primarily as a combustion zone such that the second gaseous stream includes a flue gas that includes molecular nitrogen, carbon dioxide, and water. The second gaseous stream or the second gaseous stream in which at least a portion of any fine particles, sulfur dioxide, and/or nitrogen oxides has been abated can be subjected to dehydration to produce the carbon dioxide-rich stream. The dehydration of the second gaseous stream can be carried out using any convenient system. In some embodiments, the dehydration of the second gaseous stream can be carried out according to the processes and systems disclosed in U.S. Patent Application Publication No. 2012/0060690. In some embodiments all acid gases containing $CO_2$, $SO_X$ and $NO_X$ can be sequestered together. In some embodiments, when the oxidant stream includes molecular nitrogen at a concentration of ≥15 vol %, based on the total volume of the oxidant stream, and the shifted gas stream is separated to provide the carbon dioxide-rich stream and the carbon dioxide-lean gas stream that can include molecular hydrogen and molecular nitrogen, the carbon dioxide-rich stream can optionally be further subjected to dehydration to produce a dehydrated carbon dioxide-rich stream.

In some embodiments, at least a portion of the carbon dioxide-rich stream that can be obtained from the gasification/combustion gas mixture can be utilized, upon optional compression, in an enhanced oil recovery process; sequestered, e.g., in a subterranean formation; converted into another compound; and/or introduced into a carbon dioxide pipeline.

The FIGURE depicts an illustrative system 101 for upgrading a hydrocarbon-containing feed in line 1001 by pyrolysis and gasification to produce olefins and oligomerizing at least a portion of the olefins, according to one or more embodiments. The system 101 can include one or more heating stages 1005, one or more first separation stages 1009, one or more pyrolysis zones 1021, one or more second separation stages 1031, one or more gasification/combustion zones 1041, and one or more third separation stages 1043. The system 101 can also include one or more first heat exchange stages 1047, one or more fourth separation stages 1051, and one or more compression stages 1059. The system 101 can also include one or more oligomerization zones 1067, one or more second heat exchange stages 1073, one or more regeneration zones 1079, one or more fifth separation stages 1085, and one or more hydroprocessing zones 1095.

The hydrocarbon containing feed via line 1001 can be fed into and heated within the heating stage 1005 to produce a heated feed in line 1007. In some embodiments, water, preferably in the form of steam, via line 1003 can be mixed, blended, or other combined with the hydrocarbon-containing feed in line 1001 to produce a hydrocarbon-containing feed and water mixture that can be heated in the heating stage 1005. The heated feed via line 1005 can be fed into the first separation stage 1009 to obtain a vapor fraction via line 1011 and a liquid fraction via line 1013.

In some embodiments, at least a portion of the vapor fraction via line 1011 can be fed into the pyrolysis zone 1021. In some embodiments, at least a portion of the liquid fraction via line 1013 can be fed into the pyrolysis zone 1021. In other embodiments, at least a portion of the vapor fraction via line 1011 and at least a portion of the liquid fraction via line 1013 can be fed into the pyrolysis zone 1021. In some embodiments, an optional steam stream via line 1017 can also be fed into the pyrolysis zone 1021. In a preferred embodiment, when the vapor fraction via line 1011, the liquid fraction via line 1013, and the steam stream 1017 are fed into the pyrolysis zone 1021, the vapor fraction can be fed upstream of the liquid fraction and the steam stream can be fed upstream of the liquid fraction. In addition to the vapor fraction via line 1011 and/or the liquid fraction via lien 1013, a first particle stream that can include heated particles via line 1019 can be fed into the pyrolysis zone 1021.

The vapor fraction and/or the liquid fraction and optionally the steam stream can contact the heated particles within the pyrolysis zone 1021 to effect pyrolysis of at least a portion of the hydrocarbons in the vapor fraction and/or the liquid fraction to produce a pyrolysis zone effluent. The pyrolysis zone effluent can include olefins and particles having coke deposited or otherwise formed on a surface thereof. The pyrolysis zone effluent via line 1023 can be obtained from the pyrolysis zone 1021 and fed into the second separation stage 1031. Optionally a stripping steam stream via line 1025 can be introduced into the second separation stage 1031 to improve the separation of gaseous components that can be entrained in the particles.

A first gaseous stream rich in the olefins via line 1033 and a second particle stream rich in the particles via line 1035 can be discharged or otherwise obtained from the second separation stage 1031. In some embodiments, a portion of the particles from the pyrolysis zone effluent can be recovered via line 1037 from the second separation stage 1021 and removed from the system 101. In some embodiments, it can be desirable to remove some of the particles via line 1037 and replace the removed particles with fresh or make-up particles via line 1027. For example, should the particles accumulate too much of a transition metal on the surface thereof, some of the particles can be removed via line 1037 while make-up particles can be introduced via line 1027 into the system 101.

The second particle stream via line 1035, an oxidant stream via line 1036, an optional steam stream via line 1038, an optional fuel stream via line 1039, and/or an optional diluent stream via line 1065 can be introduced or otherwise fed into the gasification/combustion zone 1041. The particles having the coke formed on the surface thereof, oxidant stream, optional steam stream, optional fuel stream, and/or optional diluent stream can be contacted within the gasification/combustion zone 1041 to effect gasification and/or combustion of at least a portion of the coke disposed on the surface of the particles to produce a gasification/combustion zone effluent. The gasification/combustion zone effluent can include heated and regenerated particles and a gasification/combustion gas mixture. In some embodiments, the gasification/combustion gas mixture can include molecular hydrogen, carbon monoxide, and carbon dioxide. In other embodiments, the gasification/combustion gas mixture can include a flue gas that can include nitrogen, carbon dioxide, and water.

In some embodiments, the gasification/combustion zone effluent can be fed into the third separation stage 1043 and a third particle stream that can include the heated and regenerated particles via line 1019 and a second gaseous stream rich in the gasification/combustion gas mixture via line 1045 can be recovered or otherwise obtained therefrom. The third separation stage 1043, as shown, can be disposed within the gasification/combustion zone 1041. However, the third separation stage 1043 can also be located outside the gasification/combustion zone 1041. The third separation stage 1043 can be an inertial separator or other separator as described above. In some embodiments, at least a portion of the third particle stream via line 1019 can be fed into the pyrolysis zone 1021 as at least a portion of the first particle stream introduced thereto.

In some embodiments, the second gaseous stream via line 1045 can be introduced into the first heat exchange stage 1047 to produce a cooled or quenched second gaseous stream via line 1049. The cooled second gaseous stream in line 1049 can be rich in the gasification/combustion zone mixture and can include condensed or liquid water. The second gaseous stream in line 1045 can be indirectly cooled by transferring heat from the second gaseous stream to a cooling medium, by direct contact with a cooling medium, or a combination thereof. In some embodiments, particles entrained in the second gaseous stream in line 1045 can also be present in the condensed water. The cooled second gaseous stream via line 1049 can be introduced or otherwise fed into the fourth separation stage 1051 to separate at least a portion of the condensed water and, if present, particles via line 1053.

In some embodiments, the fourth separation stage 1051 can include multiple separation stages. In some embodiments, the fourth separation stage 1051, in addition to removing the water and, if present, particles, can also include a hydrogen sulfide removal stage. As such, hydrogen sulfide, if present, can also be removed via line 1055 from the cooled second gaseous stream in the fourth separation stage 1051. A purified second gaseous steam via line 1057 can be recovered or otherwise obtained from the fourth separation stage 1051.

In some embodiments, the purified second gaseous stream via line 1057 can be introduced or otherwise fed into the compression stage 1059 to produce a compressed second gaseous stream via line 1061. In some embodiments, all or a portion of the compressed second gaseous stream in line 1061 can be removed from the system 101 via line 1063. In some embodiments, a portion of the compressed second gaseous stream in line 1061 can be introduced or otherwise fed via line 1065 to the gasification/combustion zone 1041 as the optional diluent stream.

In some embodiments, at least a portion of the first gaseous stream rich in the olefins via line 1033 and a first stream of oligomerization catalyst particles via line 1064 can be introduced or otherwise fed into the oligomerization zone 1067 and contacted therein under oligomerization conditions to effect oligomerization of at least a portion of the olefins in the first gaseous stream to produce an oligomerization zone effluent that can be recovered or otherwise obtained via line 1069 from the oligomerization zone 1067.

In some embodiments, the oligomerization zone 1067 can include an embedded heat exchanger 1066 located therein. Heat can be transferred away from the oligomerization zone 1067 through the embedded heat exchanger 1066 to reduce the temperature inside the oligomerization zone 1067. In some embodiments, a portion of the oligomerization catalyst particles can be withdrawn via line 1071 and introduced into the second heat exchange stage 1073 to produce a cooled oligomerization catalyst particle stream via line 1075 that can be recycled to the oligomerization zone 1067.

In some embodiments, a portion of the oligomerization catalyst particles can be withdrawn via line 1077 from the oligomerization zone 1067 that can include coke disposed thereon and introduced into the regeneration zone 1079. An oxidant stream via line 1076 and an optional fuel stream via line 1078 can also be introduced into the regeneration zone 1079. The oligomerization catalyst particles can contact the oxidant within the regeneration zone 1079 under regeneration conditions to produce regenerated oligomerization catalyst particles by combusting at least a portion of the coke disposed on the oligomerization catalyst particles. In some embodiments, at least a portion of the regenerated oligomerization catalyst particles can be reintroduced via line 1064 into the oligomerization zone 1067. In some embodiments, a regeneration zone gas mixture via line 1081 can be recovered or otherwise obtained from the regeneration zone 1079. In some embodiments, a portion of the regenerated oligomerization catalyst particles can be purged via line 1083 from the system 101 to maintain activity and fine particle content in the oligomerization catalyst within the oligomerization zone 1067.

In some embodiments, the oligomerization zone effluent via line 1069 can be introduced or otherwise fed into the fifth separation stage 1085. In some embodiments, a light gas stream via line 1087 and at least one $C_{5+}$ stream via line 1089 can be recovered or otherwise obtained from the fifth separation stage 1085. The light gas stream in line 1087 can include molecular hydrogen and one or more $C_1$-$C_4$ hydrocarbons. The $C_{5+}$ stream in line 1089 can include gasoline, a distillate, separate streams that can include gasoline and a distillate can be recovered from the fifth separation stage 1085.

In some embodiments, the $C_{5+}$ stream in line 1089 can include sulfur at a concentration of no greater than 10 ppm by weight, based on the total weight of the $C_{5+}$ hydrocarbon stream and the light gas stream in line 1087 can include hydrogen sulfide. In other embodiments, the $C_{5+}$ stream in line 1089 can include sulfur at a concentration of at least 11 ppm by weight, based on the total weight of the $C_{5+}$ hydrocarbon stream. If the $C_{5+}$ stream in line 1089 includes sulfur at a concentration of at least 11 ppm by weight, the $C_{5+}$ stream via line 1091 and molecular hydrogen via line 1093 can be fed into the optional hydroprocessing stage 1095 to produce a hydroprocessed product via line 1097. The $C_{5+}$ stream can be hydroprocessed in the hydroprocessing stage 1095 in the presence of the molecular hydrogen and a catalyst under hydroprocessing conditions sufficient to produce the hydroprocess produce in line 1097 that has a sulfur concentration of no greater than 10 ppm by weight, based on the total weight of the hydroprocessed product in line 1097.

Listing of Embodiments

This disclosure may further include the following non-limiting embodiments.

A1. A process for upgrading hydrocarbons, comprising: (I) feeding a hydrocarbon-containing feed stream comprising $C_{2+}$ hydrocarbons into a pyrolysis zone; (II) feeding a first particle stream comprising particles having a pyrolysis temperature into the pyrolysis zone; (III) contacting the hydrocarbon-containing feed stream with the particles in the pyrolysis zone under pyrolysis conditions to effect pyrolysis of at least a portion of the $C_{2+}$ hydrocarbons to produce a pyrolysis zone effluent comprising olefins and the particles, wherein coke is formed on the surface of the particles; (IV) obtaining from the pyrolysis zone effluent a first gaseous stream rich in the olefins and a second particle stream rich in the particles; (V) feeding at least a portion of the second particle stream, an oxidant stream, and optionally a first steam stream into a gasification/combustion zone; (VI) contacting the first particle stream, the oxidant stream, and optionally the first steam stream in the gasification/combustion zone under gasification/combustion conditions to produce a gasification/combustion zone effluent comprising regenerated particles and a gasification/combustion gas mixture; (VII) obtaining from the gasification/combustion zone effluent a second gaseous stream rich in the gasification/combustion gas mixture and a third particle stream rich in the regenerated particles; (VIII) feeding at least a portion of the third particle stream into the pyrolysis zone as at least a portion of the first particle stream fed into the pyrolysis zone in step (II); (IX) feeding at least a portion of the first gaseous stream into an oligomerization zone; and (X) contacting at least a portion of the first gaseous stream with oligomerization catalyst particles in the oligomerization zone under oligomerization conditions to effect oligomerization of at least a portion of the olefins in the first gaseous stream to produce an oligomerization zone effluent.

A2. The process of A1, wherein the particles in the first particle stream comprise silica, alumina, titania, zirconia, magnesia, pumice, ash, clay, diatomaceous earth, bauxite, spent fluidized catalytic cracker catalyst, or a mixture thereof; preferably the particles in the first particle stream comprise spent fluidized catalytic cracker catalyst.

A3. The process of A1 or A2, wherein in step (II), the pyrolysis temperature of the particles is in a range from 750° C. to 1,500° C., preferably from 800° C. to 1,300° C., more preferably from 800° C. to 1,100° C.

A4. The process of any of the preceding A1 to A3, wherein the particles have an average residence time in the pyrolysis zone in a range from 10 to 700 ms.

A5. The process of any of the preceding A1 to A4, wherein in step (IV) the gasification/combustion zone is located in a gasifier, and the gasification/combustion gas mixture in step (V) comprises $H_2$ and CO, and the process further comprises: (XI) obtaining a syngas stream from the second gaseous stream.

A6. The process of any of the preceding A1 to A5, wherein first gaseous stream comprises fine particles.

A7. The process of any of the preceding A1 to A6, wherein the process further comprises: (XII) separating the oligomerization zone effluent to obtain at least one of: a light gas stream comprising molecular hydrogen, and one or more of $C_1$-$C_4$ hydrocarbons; and at least one $C_{5+}$ hydrocarbon stream.

A8. The process of A7, wherein the at least one $C_{5+}$ hydrocarbon stream comprises sulfur at a concentration at no greater than 10 ppm by weight, based on the total weight of the $C_{5+}$ hydrocarbon stream, and the light gas stream comprises $H_2S$.

A9. The process of A7, wherein the at least one $C_{5+}$ hydrocarbon stream comprises sulfur at a concentration of at least 11 ppm by weight, based on the total weight of the $C_{5+}$ hydrocarbon stream, and the process further comprises: (XIII) feeding at least a portion of the $C_{5+}$ hydrocarbon stream into a hydroprocessing zone; (XIV) contacting the portion of $C_{5+}$ hydrocarbon stream with a hydroprocessing catalyst within the hydroprocessing zone under hydrodesulfurization conditions to produce a hydrodesulfurization effluent rich in hydrogen sulfide; and (XV) obtaining from the hydrodesulfurization effluent a hydrogen sulfide lean $C_{5+}$ hydrocarbon product stream.

A10. The process of any of A7 to A9, wherein the at least one $C_{5+}$ hydrocarbon stream comprises a gasoline stream and a distillate stream.

A11. The process of any of the preceding A1 to A10, wherein the hydrocarbon-containing feed stream in step (I) comprises $C_2$-$C_4$ alkanes at a total concentration of at least 10 wt %, based on the total weight of the hydrocarbon-containing feed stream.

A12. The process of any of the preceding A1 to A11, wherein the hydrocarbon-containing feed stream in step (I) comprises ethane at a concentration of at least 10 wt %, based on the total weight of the hydrocarbon-containing feed stream.

A13. The process of any of the preceding A1 to A12, wherein step (I) further comprises feeding a steam stream into the pyrolysis zone, and wherein a weight ratio of the steam stream to the $C_{2+}$ hydrocarbons in the hydrocarbon-containing feed stream is in a range from greater than zero to 2.

A14. The process of any of the preceding A1 to A13, wherein step (I) comprises: (Ia) providing a raw feed comprising $C_{2+}$ hydrocarbons; (Ib) heating the raw feed, preferably to a temperature of 325° C. to 450° C.; (Ic) separating the heated raw feed to obtain a vapor fraction and a liquid fraction; and (Id) feeding at least a portion of the vapor fraction as at least a portion of the hydrocarbon-containing feed stream in step (I) into the pyrolysis zone via a first pyrolysis feed inlet.

A15. The process of A14, wherein step (I) further comprises: (Ie) feeding at least a portion of the liquid fraction into the pyrolysis zone via a second pyrolysis feed inlet.

A16. The process of A15, wherein the second pyrolysis feed inlet is downstream of the first pyrolysis feed inlet.

A17. The process of A15 or A16, wherein a steam stream is fed into the pyrolysis zone through a steam feed inlet, and wherein the steam feed inlet is located upstream of the second pyrolysis feed inlet and optionally downstream of the first pyrolysis feed inlet.

A18. The process of A17, wherein the weight ratio of the steam stream fed through the steam feed inlet to the liquid fraction is in a range from greater than zero to 2.

A19. The process of any of the preceding A1 to A18, wherein in step (X), the oligomerization catalyst is present in a fluid bed in the oligomerization zone, and step (X) comprises: (Xa) feeding a first stream of the oligomerization catalyst particles into the oligomerization zone.

A20. The process of A19, wherein step (X) further comprises: (Xb) withdrawing a second stream of oligomerization catalyst particles from the oligomerization zone; (Xc) cooling the second stream of oligomerization catalyst particles to produce a cooled third stream of oligomerization catalyst particles; and (Xd) feeding the cooled third stream of oligomerization catalyst particles into the oligomerization zone.

A21. The process of A19 or A20, wherein step (X) further comprises: (Xe) withdrawing a fourth stream of oligomerization catalyst particles from the oligomerization zone; (Xf) regenerating the fourth stream of oligomerization catalyst particles to produce a regenerated fifth steam of oligomerization catalyst particles; and (Xg) feeding the regenerated fifth stream of oligomerization catalyst particles into the oligomerization zone.

A22. The process of any of A19 to A21, wherein step (X) further comprises: (Xh) purging a sixth stream of the oligomerization catalyst particles to maintain activity and fine particle content in the oligomerization catalyst in the oligomerization zone.

A23. The process of any of the preceding A1 to A22, wherein the oligomerization zone comprises an embedded heat exchanger located therein, and step (X) further comprises: (Xi) transferring heat away from the oligomerization zone through the embedded heat exchanger to reduce the temperature inside the oligomerization zone.

A24. The process of any of the preceding A1 to A23, wherein the oligomerization catalyst comprises a zeolite.

A25. The process of any of the preceding A1 to A24, wherein the oligomerization catalyst comprises one or more of ZSM-5, phosphorous-modified ZSM-5, and Ni-doped ZSM-5.

A26. The process of any of the preceding A1 to A25, wherein in step (X), the oligomerization conditions comprise a pressure of 100 kPa-absolute to 3,000 kPa-absolute and a temperature of 300° C. to 700° C.

A27. The process of any of the preceding A1 to A26, wherein the following is met: the pyrolysis zone is operated at a temperature of 800° C. to 1,100° C.

A28. The process of any of the preceding A1 to A27, wherein the following is met: a pressure within the pyrolysis zone is from 100 kPa-absolute to 7,000 kPa-absolute.

A29. The process of any of the preceding A1 to A28, wherein the following is met: a velocity of the gaseous components within the pyrolysis zone is in a range of 9 m/s to 155 m/s.

A30. The process of any of the preceding A1 to A29, wherein the following is met: a velocity of the particles within the pyrolysis zone is up to 15.5 m/s.

A31. The process of any of the preceding A1 to A30, wherein the following is met: a velocity of gaseous components within the pyrolysis zone is at least 20% greater than a velocity of the particles within the pyrolysis zone.

A32. The process of any of the preceding A1 to A31, wherein the following is met: a weight ratio of the particles to the hydrocarbon-containing feed stream is from 10 to 50.

A33. The process of any of the preceding A1 to A32, wherein the following is met: the pyrolysis zone effluent has a temperature in a range from 900° C. to 1,050° C. when exiting the pyrolysis zone.

A34. The process of any of the preceding A1 to A33, wherein the gasification/combustion zone is operated at a temperature in a range from 1,000° C. such as 1,200° C. to 1,500° C. and at a pressure of <800 kPa-absolute.

A35. The process of any of A1 to A33, wherein the gasification/combustion zone is operated at a temperature of at least 1,000° C. such as 1,200° C. to 1,500° C. and at a pressure of ≥800 kPa-absolute such as 800 kPa-absolute to 7,000 kPa-absolute.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for upgrading a hydrocarbon-containing feed, comprising:

(I) feeding a hydrocarbon-containing feed stream comprising $C_{2+}$ hydrocarbons into a pyrolysis zone;

(II) feeding a first particle stream comprising particles having a pyrolysis temperature into the pyrolysis zone, wherein the particles in the first particle stream comprise silica, alumina, titania, zirconia, magnesia, pumice, ash, clay, diatomaceous earth, bauxite, spent fluidized catalytic cracker catalyst, or a mixture thereof;

(III) contacting the hydrocarbon-containing feed stream with the particles in the pyrolysis zone under pyrolysis conditions to effect pyrolysis of at least a portion of the C2+ hydrocarbons to produce a pyrolysis zone effluent comprising olefins and the particles, wherein coke is formed on a surface of the particles;

(IV) obtaining from the pyrolysis zone effluent a first gaseous stream rich in the olefins and a second particle stream rich in the particles;

(V) feeding at least a portion of the second particle stream, an oxidant stream, and optionally a first steam stream into a gasification/combustion zone;

(VI) contacting the portion of the second particle stream, the oxidant stream, and optionally the first steam stream in the gasification/combustion zone under gasification/combustion conditions to produce a gasification/combustion zone effluent comprising regenerated particles and a gasification/combustion gas mixture;

(VII) obtaining from the gasification/combustion zone effluent a second gaseous stream rich in the gasification/combustion gas mixture and a third particle stream rich in the regenerated particles;

(VIII) feeding at least a portion of the third particle stream into the pyrolysis zone as at least a portion of the first particle stream fed into the pyrolysis zone in step (II);

(IX) feeding at least a portion of the first gaseous stream into an oligomerization zone; and (X) contacting at least a portion of the first gaseous stream with oligomerization catalyst particles in the oligomerization zone under oligomerization conditions to effect oligomerization of at least a portion of the olefins in the first gaseous stream to produce an oligomerization zone effluent.

2. The process of claim 1, wherein in step (II), the pyrolysis temperature of the particles is in a range from 750° C. to 1,500° C., and wherein the hydrocarbon-containing feed stream is contacted with the first particle stream in the pyrolysis zone for an average residence time in a range from 10 ms to 700 ms.

3. The process of claim 1, wherein in step (V) the gasification/combustion zone is located in a gasifier, and the gasification/combustion gas mixture in step (VI) comprises $H_2$ and CO, and the process further comprises:

(XI) obtaining a syngas stream from the second gaseous stream.

4. The process of claim 1, wherein the process further comprises:

(XII) separating the oligomerization zone effluent to obtain at least one of:

a light gas stream comprising molecular hydrogen, and one or more of $C_1$-$C_4$ hydrocarbons; and at least one $C_{5+}$ hydrocarbon stream.

5. The process of claim 4, wherein the at least one $C_{5+}$ hydrocarbon stream comprises sulfur at a concentration at no greater than 10 ppm by weight, based on the total weight of the $C_{5+}$ hydrocarbon stream, and the light gas stream comprises $H_2S$.

6. The process of claim 4, wherein the at least one $C_{5+}$ hydrocarbon stream comprises sulfur at a concentration of at least 11 ppm by weight, based on the total weight of the $C_{5+}$ hydrocarbon stream, and the process further comprises:

(XIII) feeding at least a portion of the $C_{5+}$ hydrocarbon stream into a hydroprocessing zone;

(XIV) contacting the portion of $C_{5+}$ hydrocarbon stream with a hydroprocessing catalyst within the hydroprocessing zone under hydrodesulfurization conditions to produce a hydrodesulfurization effluent rich in hydrogen sulfide; and (XV) obtaining from the hydrodesulfurization effluent a hydrogen sulfide lean $C_{5+}$ hydrocarbon product stream.

7. The process of claim 4, wherein the at least one $C_{5+}$ hydrocarbon stream comprises a gasoline stream and a distillate stream.

8. The process of claim 1, wherein the hydrocarbon-containing feed stream in step (I) comprises $C_2$-$C_4$ alkanes at a total concentration of at least 10 wt %, based on the total weight of the hydrocarbon-containing feed stream.

9. The process of claim 1, wherein step (I) further comprises feeding a steam stream into the pyrolysis zone, and wherein a weight ratio of the steam stream to the $C_{2+}$ hydrocarbons in the hydrocarbon-containing feed stream is in a range from greater than zero to 2.

10. The process of claim 1, wherein step (I) comprises:

(Ia) providing a raw feed comprising $C_{2+}$ hydrocarbons;

(Ib) heating the raw feed;

(Ic) separating the heated raw feed to obtain a vapor fraction and a liquid fraction; and (Id) feeding at least a portion of the vapor fraction as at least a portion of the hydrocarbon-containing feed stream in step (I) into the pyrolysis zone via a first pyrolysis feed inlet.

11. The process of claim 10, wherein step (I) further comprises:

(Ie) feeding at least a portion of the liquid fraction into the pyrolysis zone via a second pyrolysis feed inlet.

12. The process of claim 11, wherein the second pyrolysis feed inlet is downstream of the first pyrolysis feed inlet.

13. The process of claim 11, wherein a steam stream is fed into the pyrolysis zone through a steam feed inlet, and wherein the steam feed inlet is located upstream of the second pyrolysis feed inlet and optionally downstream of the first pyrolysis feed inlet.

14. The process of claim 1, wherein in step (X), the oligomerization catalyst is present in a fluid bed in the oligomerization zone, and step (X) comprises:

(Xa) feeding a first stream of the oligomerization catalyst particles into the oligomerization zone.

15. The process of claim 14, wherein step (X) further comprises:

(Xb) withdrawing a second stream of oligomerization catalyst particles from the oligomerization zone;

(Xc) cooling the second stream of oligomerization catalyst particles to produce a cooled third stream of oligomerization catalyst particles; and (Xd) feeding the cooled third stream of oligomerization catalyst particles into the oligomerization zone.

16. The process of claim 14, wherein step (X) further comprises:

(Xe) withdrawing a fourth stream of oligomerization catalyst particles from the oligomerization zone;

(Xf) regenerating the fourth stream of oligomerization catalyst particles to produce a regenerated fifth steam of oligomerization catalyst particles; and (Xg) feeding the regenerated fifth stream of oligomerization catalyst particles into the oligomerization zone.

17. The process of claim 14, wherein step (X) further comprises:

(Xh) purging a sixth stream of the oligomerization catalyst particles to maintain activity and fine particle content in the oligomerization catalyst in the oligomerization zone.

18. The process of claim 1, wherein the oligomerization zone comprises an embedded heat exchanger located therein, and step (X) further comprises:

(Xi) transferring heat away from the oligomerization zone through the embedded heat exchanger to reduce the temperature inside the oligomerization zone.

19. The process of claim 1, wherein the oligomerization catalyst comprises a zeolite.

20. The process of claim 1, wherein in step (X), the oligomerization conditions comprise a pressure of 100 kPa-absolute to 3,000 kPa-absolute and a temperature of 300° C. to 700° C.

21. The process of claim 1, wherein:

the pyrolysis zone is operated at a temperature of 800° C. to 1,100° C.;

a pressure within the pyrolysis zone is from 100 kPa-absolute to 7,000 kPa-absolute;

a velocity of the gaseous components within the pyrolysis zone is in a range of 9 m/s to 155 m/s;

a velocity of the particles within the pyrolysis zone is up to 15.5 m/s;

a velocity of gaseous components within the pyrolysis zone is at least 20% greater than a velocity of the particles within the pyrolysis zone;

a weight ratio of the particles to the hydrocarbon-containing feed stream is from 10 to 50; and the pyrolysis zone effluent has a temperature in a range from 900° C. to 1,050° C. when exiting the pyrolysis zone.

22. The process of claim 1, wherein the particles in the first particle stream comprise spent fluidized catalytic cracker catalyst.

23. A process for upgrading a hydrocarbon-containing feed, comprising:

(Ia) providing a raw feed comprising $C_{2+}$ hydrocarbons;

(Ib) heating the raw feed;

(Ic) separating the heated raw feed to obtain a vapor fraction and a liquid fraction;

(Id) feeding at least a portion of the vapor fraction as a hydrocarbon-containing feed stream into a pyrolysis zone via a pyrolysis feed inlet, wherein the vapor fraction comprises $C_{2+}$ hydrocarbons;

(II) feeding a first particle stream comprising particles having a pyrolysis temperature into the pyrolysis zone;

(III) contacting the hydrocarbon-containing feed stream with the particles in the pyrolysis zone under pyrolysis conditions to effect pyrolysis of at least a portion of the C2+ hydrocarbons to produce a pyrolysis zone effluent comprising olefins and the particles, wherein coke is formed on a surface of the particles;

(IV) obtaining from the pyrolysis zone effluent a first gaseous stream rich in the olefins and a second particle stream rich in the particles;

(V) feeding at least a portion of the second particle stream, an oxidant stream, and optionally a first steam stream into a gasification/combustion zone;

(VI) contacting the portion of the second particle stream, the oxidant stream, and optionally the first steam stream in the gasification/combustion zone under gasification/combustion conditions to produce a gasification/combustion zone effluent comprising regenerated particles and a gasification/combustion gas mixture;

(VII) obtaining from the gasification/combustion zone effluent a second gaseous stream rich in the gasification/combustion gas mixture and a third particle stream rich in the regenerated particles;

(VIII) feeding at least a portion of the third particle stream into the pyrolysis zone as at least a portion of the first particle stream fed into the pyrolysis zone in step (II);

(IX) feeding at least a portion of the first gaseous stream into an oligomerization zone; and (X) contacting at least a portion of the first gaseous stream with oligomerization catalyst particles in the oligomerization zone under oligomerization conditions to effect oligomerization of at least a portion of the olefins in the first gaseous stream to produce an oligomerization zone effluent.

24. A process for upgrading a hydrocarbon-containing feed, comprising:

(I) feeding a hydrocarbon-containing feed stream comprising $C_{2+}$ hydrocarbons into a pyrolysis zone;

(II) feeding a first particle stream comprising particles having a pyrolysis temperature into the pyrolysis zone;

(III) contacting the hydrocarbon-containing feed stream with the particles in the pyrolysis zone under pyrolysis conditions to effect pyrolysis of at least a portion of the C2+ hydrocarbons to produce a pyrolysis zone effluent comprising olefins and the particles, wherein coke is formed on a surface of the particles;

(IV) obtaining from the pyrolysis zone effluent a first gaseous stream rich in the olefins and a second particle stream rich in the particles;

(V) feeding at least a portion of the second particle stream, an oxidant stream, and optionally a first steam stream into a gasification/combustion zone;

(VI) contacting the portion of the second particle stream, the oxidant stream, and optionally the first steam stream in the gasification/combustion zone under gasification/combustion conditions to produce a gasification/combustion zone effluent comprising regenerated particles and a gasification/combustion gas mixture;

(VII) obtaining from the gasification/combustion zone effluent a second gaseous stream rich in the gasification/combustion gas mixture and a third particle stream rich in the regenerated particles;

(VIII) feeding at least a portion of the third particle stream into the pyrolysis zone as at least a portion of the first particle stream fed into the pyrolysis zone in step (II);

(IX) feeding at least a portion of the first gaseous stream into an oligomerization zone;

(X) feeding a first stream of oligomerization catalyst particles and at least a portion of the first gaseous steam into an oligomerization zone;

(XI) contacting at least a portion of the first gaseous stream with the first stream of oligomerization catalyst particles in the oligomerization zone under oligomerization conditions to effect oligomerization of at least a portion of the olefins in the first gaseous stream to produce an oligomerization zone effluent, wherein the oligomerization catalyst is present in a fluid bed in the oligomerization zone;

(XII) withdrawing a second stream of oligomerization catalyst particles from the oligomerization zone;

(XIII) cooling the second stream of oligomerization catalyst particles to produce a cooled third stream of oligomerization catalyst particles; and (XIV) feeding the cooled third stream of oligomerization catalyst particles into the oligomerization zone.

* * * * *